United States Patent
Hilbig et al.

(10) Patent No.: US 10,517,526 B2
(45) Date of Patent: Dec. 31, 2019

(54) SLEEP MONITORING

(71) Applicant: KONINKLIJKE PHILIPS N.V., Eindhoven (NL)

(72) Inventors: Rainer Hilbig, Aachen (DE); Peter Hermanus Bouma, Maaseik (BE); Jing Su, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/321,754

(22) PCT Filed: Oct. 24, 2017

(86) PCT No.: PCT/EP2017/077041
§ 371 (c)(1),
(2) Date: Jan. 29, 2019

(87) PCT Pub. No.: WO2018/082959
PCT Pub. Date: May 11, 2018

(65) Prior Publication Data
US 2019/0246974 A1    Aug. 15, 2019

(30) Foreign Application Priority Data

Nov. 2, 2016 (WO) ............... PCT/CN2016/000596
Feb. 7, 2017 (EP) .................... 17154976

(51) Int. Cl.
*A61B 5/00* (2006.01)
*A61B 5/083* (2006.01)

(52) U.S. Cl.
CPC .......... *A61B 5/4809* (2013.01); *A61B 5/0836* (2013.01); *A61B 5/7203* (2013.01);
(Continued)

(58) Field of Classification Search
CPC ...... A61B 5/0836; A61B 5/4806–4818; A61B 5/7239
See application file for complete search history.

(56) References Cited

U.S. PATENT DOCUMENTS

| 7,396,331 | B2 | 7/2008 | Mack |
| 2005/0124864 | A1 | 6/2005 | Mack |

(Continued)

FOREIGN PATENT DOCUMENTS

| CN | 203101953 U | 7/2013 |
| EP | 2929837 A1 | 10/2015 |

(Continued)

*Primary Examiner* — Daniel L Cerioni
*Assistant Examiner* — Raymond P Dulman

(57) ABSTRACT

A sleep monitoring system (10) for monitoring the sleep of a pair of subject comprises a pair of CO2 sensors (21,21') for mounting in different sleeping regions within a space (1) and a processor (31) communicatively coupled to the pair of CO2 sensors. The processor is adapted to, for each CO2 sensor in a particular sleeping region, monitor (203) a CO2 concentration from sensor data produced by the CO2 sensor in said particular sleeping region to detect a presence of a subject in said sleeping region; to register (207) the monitored CO2 concentration upon detecting (205) said presence; to determine (303) a degree of crosstalk between said CO2 sensors upon detecting said presence; and to derive (305, 313) sleep pattern information for said subject from the registered CO2 concentration during said presence as a function of the determined degree of crosstalk, wherein the sleep pattern information comprises at least an indication that the subject is awake and an indication that the subject is asleep.

15 Claims, 10 Drawing Sheets

(52) U.S. Cl.
CPC .......... *A61B 5/7239* (2013.01); *A61B 5/4815* (2013.01); *A61B 5/6891* (2013.01)

(56) References Cited

U.S. PATENT DOCUMENTS

| | | |
|---|---|---|
| 2013/0096404 A1 | 4/2013 | Colman |
| 2015/0173671 A1 | 6/2015 | Paalasmaa |
| 2016/0317781 A1* | 11/2016 | Proud .................... A61M 21/02 |
| 2016/0324466 A1* | 11/2016 | Chang .................. A61B 5/4818 |
| 2019/0069840 A1* | 3/2019 | Young .................. A61B 5/0205 |

FOREIGN PATENT DOCUMENTS

| | | |
|---|---|---|
| EP | 2976994 A2 | 1/2016 |
| WO | 2017006204 A1 | 1/2017 |
| WO | 2017194450 A1 | 11/2017 |

* cited by examiner

SLEEP MONITORING

This application is the U.S. National Phase application under 35 U.S.C. § 371 of International Application No. PCT/EP2017/077041, filed on Oct. 24, 2017, which claims the benefit of International Application No. PCT/CN2016/000596 filed on Nov. 2, 2016 and International Application No. 17154976.9 filed on Feb. 7, 2017. These applications are hereby incorporated by reference herein.

FIELD OF THE INVENTION

The present invention relates to a sleep monitoring system for monitoring the sleep of a pair of subjects.

The present invention further relates to a method of monitoring the sleep of a pair of subjects.

The present invention yet further relates to a computer program product that facilitates the monitoring of the sleep of a pair of subjects.

BACKGROUND OF THE INVENTION

US 2015173671 A1 discloses a method and system of physiological monitoring. The method includes the steps of: measuring a quantity relating to a first subject with a first sensor positioned in or in proximity of the first subject and configured to provide a first signal, measuring a quantity relating to a second subject with a second sensor positioned in or in proximity of the second subject and configured to provide a second signal, and analyzing the first and the second signal and the interrelation of the first and second signal in order to determine at least one event relating to the first and/or the second subject.

EP 2976994 A2 discloses a sleep assist system to monitor and assist the user's sleep. The system comprises: a bedside device adapted to be positioned near the user's bed, the bedside device optionally comprising a loudspeaker, a light source, a microphone, a light sensor, a temperature sensor, a control unit, an air quality sensor, a display unit, a user interface. The system further comprises a first sensing unit positioned in the user's bed comprising one or more sensors adapted to sense at least pressure and changes in pressure exerted by the user lying in the bed. An additional sensor device is in contact with the user's body, and coupled to the bedside device. The system is configured to correlate the data obtained from both the first sensing unit and the additional sensor device.

Sleep is a critical part of our lives. It ensures that our bodies rest and can repair and is therefore crucial for long-term health. It is therefore important that people, i.e. subjects, sleep properly. Without proper sleep, chronic health issues may arise. For this reason, many solutions have been proposed that facilitate the monitoring of sleep by a subject, for example to diagnose sleep disorders or to improve the sleep process by creating an atmosphere in a confined space in which the subject is sleeping to improve the quality of sleep for that subject.

For example, CN 203101953 A discloses a device that comprises a brainwave detecting means to detect the brainwaves of a subject and a controller arranged to analyze these brainwaves to detect various sleep stages, with the device arranged to control an air conditioner, humidifier and/or lighting controller to improve the sleep of that subject in response to a detected sleep stage.

A drawback of this device is that it requires physical contact with the subject attempting to sleep. Similar solutions, e.g. solutions in which pressure sensors or the like are fitted to a mattress on which a subject is attempting to sleep, to an extent suffer from the same problem or may suffer from accuracy problems. This physical contact can be perceived as uncomfortable and as such cause a disruption of the sleep of the subject being monitored. Hence, there exists a need for a sleep monitoring system that can monitor sleep in a more unobtrusive manner. In particular, there exists a need for a sleep monitoring system that can accurately monitor sleep of a pair of subjects, e.g. a couple sharing a bed, in an unobtrusive manner.

SUMMARY OF THE INVENTION

The present invention seeks to provide a sleep monitoring system that does not require physical contact with the pair of subjects sleeping to obtain accurate sleep information.

The present invention further seeks to provide a method of monitoring the sleep of a pair of subjects that does not require physical contact with the subjects sleeping to obtain accurate sleep information.

The present invention yet further seeks to provide a computer program product that facilitates the implementation of such a method on a computing device.

According to an aspect, there is provided a sleep monitoring system for monitoring the sleep of a pair of subjects, comprising a pair of $CO_2$ sensors for mounting in different sleeping regions within a space and a processor communicatively coupled to the pair of $CO_2$ sensors, wherein the processor is adapted to, for each $CO_2$ sensor in a particular sleeping region, monitor a $CO_2$ concentration from sensor data produced by the $CO_2$ sensor in said particular sleeping region to detect a presence of a subject in said sleeping region; register the monitored $CO_2$ concentration upon detecting said presence; determine a degree of crosstalk between said $CO_2$ sensors upon detecting said presence; and derive sleep pattern information for said subject from the registered $CO_2$ concentration during said presence as a function of the determined degree of crosstalk, wherein the sleep pattern information comprises at least an indication that the subject is awake and an indication that the subject is asleep.

The present invention is based on the insight that the sleep of a pair of subjects, i.e. a pair of individuals sharing a such as a bedroom may be determined in an unobtrusive manner using a pair of $CO_2$ sensors, each dedicated to one of the subjects. It has been found that such $CO_2$ sensors can facilitate the accurate determination of sleep data for each individual, e.g. sleep efficiency data, in particular when crosstalk between the $CO_2$ sensors is quantified. Particularly, it has been found that crosstalk between $CO_2$ sensors cannot be ignored if ventilation of the shared space, e.g. through opening one or more doors or windows, is insufficient. Therefore, embodiments of the present invention seek to determine the degree of ventilation of the shared space in order to determine whether crosstalk between these $CO_2$ sensors must be determined in order to obtain accurate sleep data for the respective individuals in the space with these sensors.

To this end, the sleep monitoring system may be adapted to receive user information, e.g. a user instruction, indicative of a degree of ventilation of the shared space, for example from a user interface forming part of the sleep monitoring system or from a user device communicatively coupled to the sleep monitoring system such as a smart phone, tablet computer, or the like. Such a user information for example may comprise an indication of which doors or windows of the shared space have been opened such that the sleep monitoring system may estimate the degree of ventilation of the shared space from the provided user information in order to determine whether the CO2 sensor data of the respective CO2 sensors requires correction for crosstalk between these sensors. Such estimation may be based on historical calibration data of the sleep monitoring system, for instance by determining for each door or window of the shared space its ventilation efficiency by opening that door or window and monitoring the development of CO2 levels within the space when one or more subjects are present.

Alternatively, the processor may be adapted to determine a minimum CO2 concentration and a maximum CO2 concentration in the monitored CO2 concentration and ignore said crosstalk in deriving the sleep pattern for said subject if a difference between the minimum CO2 concentration and the maximum CO2 concentration is below a defined threshold. This has the advantage that the sleep monitoring system can automatically determine whether crosstalk between the CO2 sensors needs to be considered, thereby obviating the need for user intervention.

In order to determine the sleep efficiency of a subject in the space, the processor may be adapted to derive sleep pattern information for said subject from the registered CO2 concentration by identifying that the subject is awake when a rate of increase in said registered CO2 concentration is greater than a first threshold; identifying a light sleep phase of the subject when a rate of increase in said registered $CO_2$ concentration is between the first threshold and a second threshold; and identify a deep sleep phase of the subject when a rate of increase in said registered $CO_2$ concentration is below the second threshold. For example, the processor may be adapted to determine the first threshold by in situ calibration of the sleep monitoring system. By evaluating the CO2 concentration information provided by the respective CO2 sensors in this manner, the sleep efficiency of a subject monitored with a particular CO2 sensor may be accurately determined.

To this end, the processor may be adapted to, for each CO2 sensor in a particular sleeping region, initiate a period during which the CO2 concentration is monitored for sleep evaluation purposes upon detection of said presence; terminate said period upon detection of said subject leaving said particular sleeping region; and determine at least one rate of CO2 concentration change during said period. For example, the processor may be adapted to store CO2 data captured with the CO2 sensors during this period only, as only this data is relevant to the determination of the sleep efficiency of the one or more subjects sleeping in the shared space.

In some embodiments, the sleep monitoring system may comprise one or more additional sensors, e.g. motion detection sensors, optical sensors, temperature sensors, or the like, adapted to detect the presence of one or more subjects within the shared space. Alternatively, the processor may be adapted to detect said presence by detection of an increase in the CO2 concentration in said particular region exceeding a first further threshold; and detect said subject leaving said particular sleeping region by detection of a decrease in the CO2 concentration exceeding a second further threshold, which has the advantage that no additional sensors are required, thereby reducing the cost of the sleep monitoring system.

In an embodiment, the processor is adapted to, for each CO2 sensor, periodically sample the CO2 concentration in said particular sleeping region; and derive the at least one rate of CO2 concentration change in the registered CO2 concentration by a linear fit based on the periodic CO2 concentration samples taken during registering said CO2 concentration. This for example may be done by the processor periodically sampling the CO2 concentration at a point in time by averaging a plurality of CO2 measurements with the CO2 sensor in said particular sleeping region in a time period associated with said point in time, said time period being at most half a sampling period of the periodic sampling in order to improve the accuracy of each sample.

In an embodiment, the linear fit may be used to determine the crosstalk between the CO2 sensors of the sleep monitoring system. In such a scenario, the processor may be further adapted to, for each registered monitored CO2 concentration, determine a difference function between an actual monitored CO2 concentration and said linear fit; and determine a crosstalk contribution to said registered monitored CO2 concentration based on a difference between the difference function of said registered monitored CO2 concentration and a product of an averaged difference function of the other registered monitored CO2 concentration and a scaling factor, said scaling factor being dependent of at least one of a volume of said space and a rate of ventilation of said space.

The processor may be further adapted to monitor a CO2 concentration from sensor data produced by both CO2 sensors upon detecting the presence of a subject in one of said sleeping regions.

According to another aspect, there is provided a method for monitoring the sleep of a pair of subjects in different sleeping regions within a space, each sleeping region comprising a CO2 sensor, the method comprising, for each CO2 sensor, monitoring a CO2 concentration from sensor data produced by the CO2 sensor in said particular sleeping region to detect a presence of a subject in said sleeping region; registering the monitored CO2 concentration upon detecting said presence; determining a degree of crosstalk between said CO2 sensors upon detecting said presence; and deriving sleep pattern information for said presence from the registered CO2 concentration during said presence as a function of the determined degree of crosstalk, wherein the sleep pattern information comprises at least an indication that the subject is awake and an indication that the subject is asleep. Such a method may be used to accurately determine sleep pattern information for a couple sharing the same space in an unobtrusive manner by factoring in crosstalk between the CO2 sensors when necessary.

The method may further comprise, for each CO2 sensor in a particular region, initiating a period during which the CO2 concentration is monitored for sleep evaluation purposes upon detecting (said presence, preferably by detection of an increase in the CO2 concentration in said particular region exceeding a first further threshold; terminating said period upon detecting said presence leaving said particular region, preferably by detection of a decrease in the CO2 concentration exceeding a second further threshold; and determining at least one rate of CO2 concentration change during said period. This facilitates active monitoring of CO2 concentrations in the space when the space is occupied by the pair of subjects (or by one of the subjects), thereby improving the efficiency of the method. In an embodiment, the method further comprises periodically sampling the CO2 concentration in said particular region, preferably by averaging a plurality of CO2 measurements with the CO2 sensor in said particular region in a time period associated with said point in time, said time period being at most half a sampling period of the periodic sampling; and deriving the at least one rate of CO2 concentration change in the registered CO2 concentration by a linear fit based on the periodic CO2 concentration samples taken during registering said CO2 concentration. Such a linear fit may be used by the method to estimate a degree of crosstalk between the CO2 sensors. In an example embodiment, the method further comprises, for each registered CO2 concentration, determining a difference function between an actual monitored CO2 concentration and said linear fit; and determining a crosstalk contribution to said registered monitored CO2 concentration based on a difference between the difference function of said registered monitored CO2 concentration and a product of an averaged difference function of the other registered monitored CO2 concentration and a scaling factor, said scaling factor being dependent of at least one of a volume of said space and a rate of ventilation of said space.

According to yet another aspect, there is provided a computer program product comprising a computer readable storage medium having computer readable program instructions embodied therewith for, when executed on a processor of a sleep monitoring system according to any embodiment of the present invention, cause the processor to implement the method according to any embodiment of the present invention.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
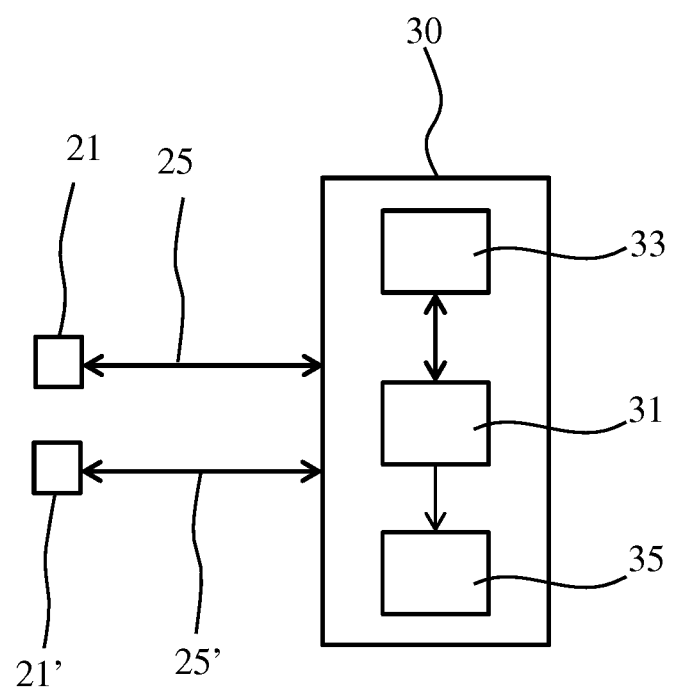
FIG. 1 schematically depicts a sleep monitoring system according to an embodiment.

It should be understood that the Figures are merely schematic and are not drawn to scale. It should also be understood that the same reference numerals are used throughout the Figures to indicate the same or similar parts.

Figure 2:
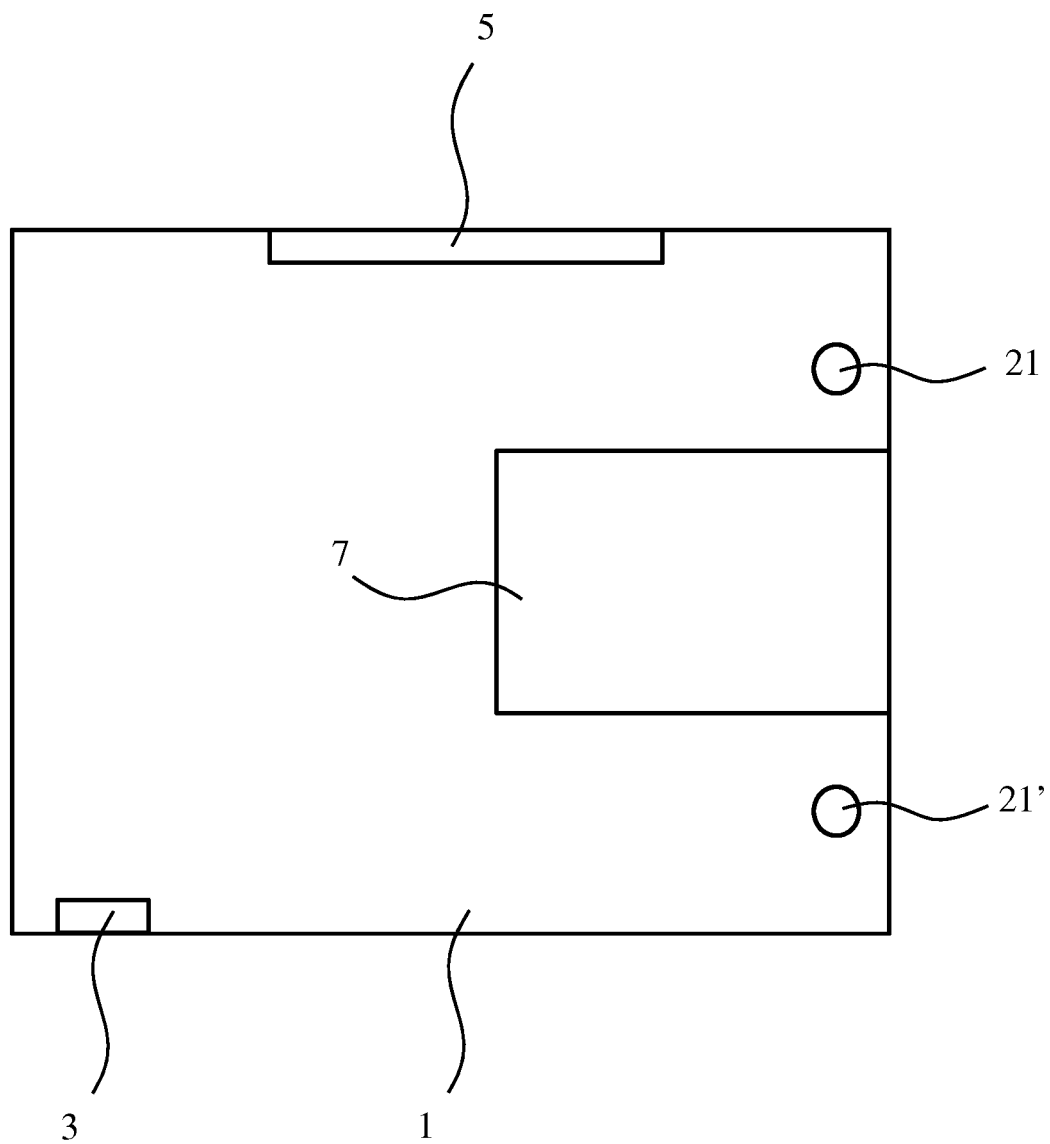
FIG. 2 schematically depicts a sleep monitoring system according to an embodiment deployed in a space for sleeping.

FIG. 1 schematically depicts a sleep monitoring system 10 according to an embodiment. The sleep monitoring system 10 is adapted to monitor the sleep of a pair of subjects in a confined space 1 as schematically depicted in FIG. 2, such as a bedroom in which a pair of CO2 sensors 21, 21' of the sleep monitoring system 10 are positioned such that each CO2 sensor 21, 21' is within detection range ($S_p$) of a subject to be monitored, e.g. with 1 m of such a subject. For example, the CO2 sensors 21, 21' may be positioned on either side of a (double) bed 7 within the space 1 such that each sensor is positioned to detect CO2 emissions by the subject (person) sleeping on that side of the bed 7. The CO2 sensor 21, 21' may be positioned in any suitable manner, e.g. attached to a headboard, post or frame of the bed 7. A distance between the CO2 sensors 21, 21' preferably is at least the detection range $S_p$ and is preferably larger than this detection range to limit the amount of crosstalk between the CO2 sensors 21, 21'. Each of the CO2 sensors 21, 21' should be positioned away from ventilation outlets 3, 5, e.g. doors or windows, of the space 1 as direct exposure to such ventilation may cause a deterioration in the accuracy of the CO2 readings provided by such CO2 sensors 21, 21'. For example, each CO2 sensor may be positioned at a distance from such ventilation outlets that is larger than the detection range $S_p$ to avoid interference from such ventilation.

The CO2 sensors 21, 21' may be stand-alone sensors or may be integrated in one or more sensor devices (not shown). For example, each CO2 sensor may be integrated in a separate sensor device or both CO2 sensors 21, 21' may be integrated in the same sensor device. Such a sensor device 20 may further comprise one or more further sensors (not shown), which may include a light sensor, a sound sensor, e.g. a microphone, a user input sensor, e.g. a user interface, and so on. Such a sensor device may be a stand-alone device, e.g. a sensor box or the like that may be positioned in close vicinity to the subject to be monitored. For example, the sensor device may be dimensioned such that it can be clipped or otherwise secured to the bed 7, e.g. to a headboard of the bed, in which the one or more subjects sleep, such that a change in the $CO_2$ concentration caused by exhalation of $CO_2$ by the one or more subjects can be accurately monitored with the sensor device before the $CO_2$ diffuses into the total volume of air within the confined space 1 in which the sensor device is positioned, e.g. a bedroom in which the one or more subjects sleep.

In alternative embodiments, such a sensor device may form part of an apparatus adapted to alter the condition of the atmosphere within the confined space as will be explained in more detail below. For example, such an apparatus may be adapted to adjust at least one of the purity, humidity, temperature and scent level in the atmosphere (air) in the confined space. Such functionality for example may be included in an air purification apparatus, an air conditioning apparatus, an air humidification apparatus, a scent release apparatus or any apparatus that includes one or more of the above functionality.

The sleep monitoring system 10 typically comprises a computing device 30 including a processor 31. As shown in FIG. 1, the computing device 30 may be a separate device to CO2 sensors 21, 21', e.g. when integrated into one or more sensor devices. For example, the computing device 30 may be any suitable computing device, such as a personal computer, e.g. a desktop computer or a laptop computer, a tablet computer, a personal digital assistant, a mobile communication device such as a smartphone, a wearable smart device such as a smart watch, and so on. The computing device 30 may form an assembly with the CO2 sensors 21, 21', e.g. with one or more sensor devices including the CO2 sensors 21, 21'. In such an assembly, the computing device 30 may be a discrete entity or may form part of an apparatus adapted to alter the condition of the atmosphere within the confined space, i.e. such an apparatus may comprise the processor 31. The processor 31 may be any suitable processor, e.g. a generic processor or an application-specific processor. The computing device 30 may further comprise a data storage device 33 communicatively coupled to the processor 31.

The computing device 30 is arranged to communicate with the CO2 sensors 21, 21' to obtain CO2 levels in the confined space 1 in which the one or more subjects are located. The CO2 sensors 21, 21' and the further sensor(s) if present may be communicatively coupled to the computing device 30 over respective communication links 25, 25' (or over a shared communication link) such that the processor 31 can receive sensor readings from such sensors. Such a communication link may be a wired communication link, e.g. in case the sensors are integral to the computing device 30, or may be a wireless communication link, e.g. in case the sensors are located in a different device to the computing device 30, e.g. in a separate sensor device as previously explained. To this end, the respective devices communicatively coupled over such a wireless communication link may include a wireless transceiver (not shown). The devices may communicate with each other through their respective wireless transceivers using any suitable wireless communication protocol, e.g. Bluetooth, Wi-Fi, a mobile communication protocol such as 2G, 3G, 4G or 5G, a suitable near-field communication (NFC) protocol or a proprietary protocol. In case of such wireless communication, the respective devices may communicate directly with each other or may communicate with each other through an intermediary such as a wireless bridge, a router, a hub, and so on. Any suitable embodiment of wired or wireless communication between such respective devices may be contemplated.

The processor 31 may be further communicatively coupled to a data storage device 33, here shown to form part of the computing device 30. Such a data storage device may be any suitable device for storing digital data, e.g. a random access memory, a cache memory, a Flash memory, a solid state storage device, a magnetic storage device such as hard disk, an optical storage device and so on. Alternatively, the data storage device 33 may be separate from the computing device 30, e.g. a network storage device or a cloud storage device accessible to the processor 31 over a network such as a LAN or the Internet. The processor 31 may store sensor data received from the connected CO2 sensors 21, 21' in the data storage device in order to collect and store historical sleep information obtained for the subjects in the confined space, for example to analyze the sleep efficiency of these subjects as will be explained in more detail below.

The computing device 30 may further comprise a sensory output device 35 under control of the processor 31. Such a sensory output device may be any device that capable of producing an output that can be detected by one of the human senses. For example, the sensory output device 35 may be adapted to produce a visible or audible output. The processor 31 may be adapted to generate a control signal indicative of a determined sleep efficiency of the subject with the processor 31, which control signal triggers the sensory output device 35 to produce a sensory output indicating the determined sleep efficiency for a particular subject. For example, the sensory output device 35 may comprise a display adapted to display the determined sleep efficiency (or sleep efficiency history) of such a subject.

Figure 3:
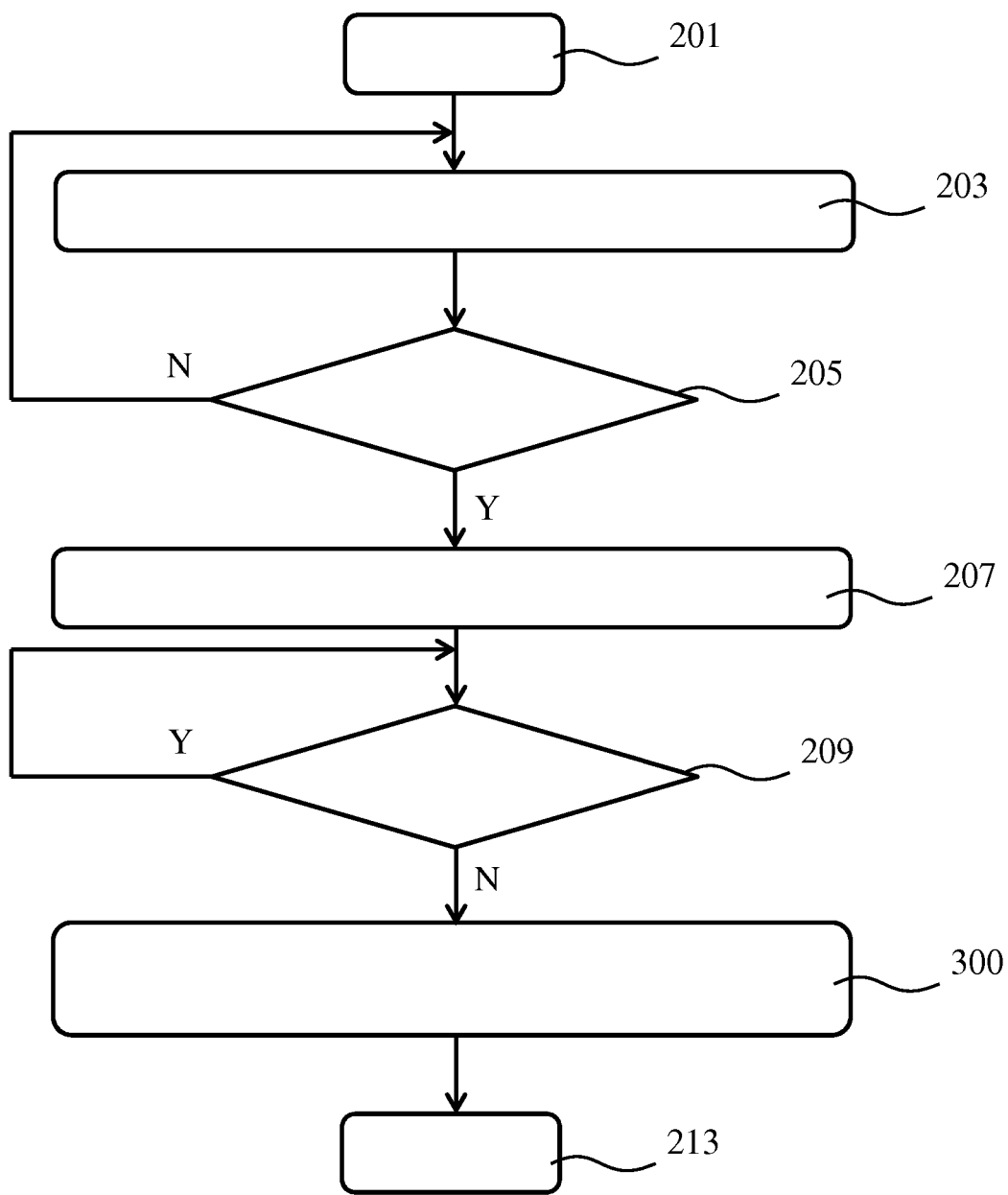
FIG. 3 is a flowchart of a sleep monitoring method according to an embodiment.

The sleep monitoring system 10 in an embodiment implements the sleep monitoring method 200, a flowchart of which is depicted in FIG. 3. The method 200 starts in 201, e.g. by switching on the sleep monitoring system 10, after which the method 200 proceeds to 203 in which CO2 levels in the space 1 are monitored with the CO2 sensors 21, 21'. Such CO2 sensors preferably have a sensitivity of better than 100 ppm and more preferably have an absolute accuracy of better than 10 ppm. The sleep monitoring system 10 preferably is configured to sample CO2 levels in the space 1 at a sampling rate (SR) of at least 10 samples per hour, more preferably at least 50 samples per hour. Each sampled CO2 level, i.e. CO2 concentration, may be based on a plurality of CO2 measurements with the CO2 sensors 21, 21', in which the sampled value is the average of the plurality of CO2 measurements. Such averaging reduces the risk of sampled values being corrupted by noise, as such noise is typically averaged out in such an averaging technique.

Periodically, the sampled data is evaluated for the purpose of determining the sleep efficiency of the one or more subjects sleeping in the space 1. Such a period may be predefined, e.g. once-a-day at a set time of day or in response to the detection of a subject waking up, or may be triggered by a user command provided to the sleep monitoring system 10, e.g. using any suitable user interface, e.g. a user interface forming part of the sleep monitoring system 10 or communicatively coupled to the sleep monitoring system 10 such as the user interface of a mobile communication device such as a smart phone, a tablet computer, a personal computer, a laptop computer, and so on. In evaluation mode, the processor 31 evaluates the raw data collected with the CO2 sensors 21, 21' and/or additional sensors such as any suitable subject presence detection sensors as previously explained, to determine at which point a subject has entered the space 1, as indicated by 205. For example, such presents may be detected with the CO2 sensors 21, 21' by detection of a sudden increase in the CO2 levels within the space 1, as such a sudden increase indicates exhalation of CO2 by a subject within the space 1. In an embodiment, the processor 31 is adapted to determine the presence of such a subject by checking if the actual CO2 level at time t as determined with a CO2 sensor 21, 21' is larger than the product of a reference CO2 level at time to and scaling factor FTF:

$$CO2(t) > FTF * CO2(t_0) \qquad (1)$$

The scaling factor FTF may be empirically determined and is typically chosen such that the presence of the subject is determined with high accuracy, i.e. the risk of false positives or false negatives in the presence detection is minimized. For example, a typical value for FTF is 1.3 although other values equally may be applicable, as it will be readily understood by the skilled person that the appropriate value for FTF depends from a number of factors, e.g. the volume of the space 1 and the level of ventilation in the space 1. The value of the scaling factor FTF can also be improved or adapted by "learning" from the CO2 time development measured over several time intervals, e.g. several nights.

Upon determining the presence of a subject within the space 1, e.g. by determining that equation (1) is true or by detection of the subject with a presence detector, the method 200 proceeds to 207 in which the processor 31 initiates an evaluation period of the data collected with the CO2 sensor 21, 21', which as will be readily understood by the skilled person, may involve separate evaluation of the data collected with the respective CO2 sensors 21, 21' in order to determine individual sleep efficiency data for the subjects sleeping in the space 1. In 209, the processor 31 progresses through the sensor data collected with the computing device 30 to determine if the subject of interest is still present in the space 1. The departure of the subject from the space 1 may be detected with the presence detectors (if present in the sleep monitoring system 10) or with the CO2 sensor 21, 21' by checking if the actual CO2 level at time $t_1$ as determined with a CO2 sensor 21, 21' is larger than the product of a reference CO2 level at time t at a defined time period before $t_1$, e.g. $t=t_1-15$ min and a further scaling factor STF:

$$CO2(t_1) < STF*CO2(t) \quad (2)$$

The scaling factor STF may be empirically determined and is typically chosen such that the departure of the subject from the space 1 is determined with high accuracy, i.e. the risk of false positives or false negatives in the departure detection is minimized. For example, a typical value for STF is 0.9 although other values equally may be applicable, as it will be readily understood by the skilled person that the appropriate value for STF depends from a number of factors, e.g. the volume of the space 1 and the level of ventilation in the space 1. The value of the scaling factor STF can also be improved or adapted by "learning" from the CO2 time development measured over several time intervals, e.g. several nights.

Upon determining the departure of the subject from the space 1, the method 200 proceeds to sleep efficiency monitoring method 300 in which the endpoint of the evaluation period is set to $t_1$ and the CO2 data collected during the evaluation period is evaluated to derive the sleep efficiency of the subject over the period $t-t_1$, as will be explained in further detail below. The method 200 at this point may revert back to 203 to continue evaluation of the data collected with the computing device 30, e.g. in order to detect a further evaluation period in the data for which sleep efficiency evaluation may be performed or alternatively the method 200 at this point may terminate in 213.

The sleep efficiency monitoring method 300 starts in 301, e.g. by method 200 entering the sleep efficiency monitoring method 300 from evaluation 209, after which the sleep efficiency monitoring method 300 proceeds to 303 in which an evaluation is performed of the need to correct the CO2 data collected with the respective CO2 sensors 21, 21' for crosstalk between these sensors. In an embodiment, this involves evaluation of the ventilation conditions of the space 1, as sufficient ventilation of such a space has been found to suppress crosstalk between CO2 sensors 21, 21' to such an extent that it may be ignored. In an embodiment, the sleep monitoring system 10 is adapted to determine the ventilation conditions of the space 1 from user information provided by a user through a user interface of the sleep monitoring system 10 or a user interface of a separate device in (wireless) communication with the sleep monitoring system 10 as previously explained.

For example, such user information may provide an indication of which of the doors 3 or windows 5 have been opened, based on which the sleep monitoring system 10 may determine if the crosstalk between CO2 sensors 21, 21' may be ignored. The sleep monitoring system 10, i.e. the processor 31, may base such a determination on historical calibration data in which CO2 levels within the space 1 (in the presence of a defined number of subjects) were collected with the CO2 sensors 21, 21' with one or more of the doors 3 and windows 5 opened, to determine whether the ventilation of the space 1 under such defined ventilation conditions is sufficient to suppress crosstalk between the CO2 sensors 21, 21'. An indication of such crosstalk becoming non-negligible may be determined by determining a difference $\Delta p$ between the maximum CO2 level MAX(CO2(t)) and the minimum CO2 level MIN(CO2(t)), e.g. within an aforementioned evaluation period:

$$\Delta p = MAX(CO2(t)) - MIN(CO2(t)) \quad (3)$$

and determining if this difference is below a defined threshold T, e.g. 150 ppm. In case this difference is below the defined threshold T, the method 300 proceeds to 305 in which the sleep efficiency evaluation for each subject in the space 1 is based on the uncorrected CO2 data collected with the CO2 sensor 21, 21' associated with that subject, i.e. based on the isolated CO2 data collected with that sensor without factoring in crosstalk with the other CO2 sensor.

Figure 5:
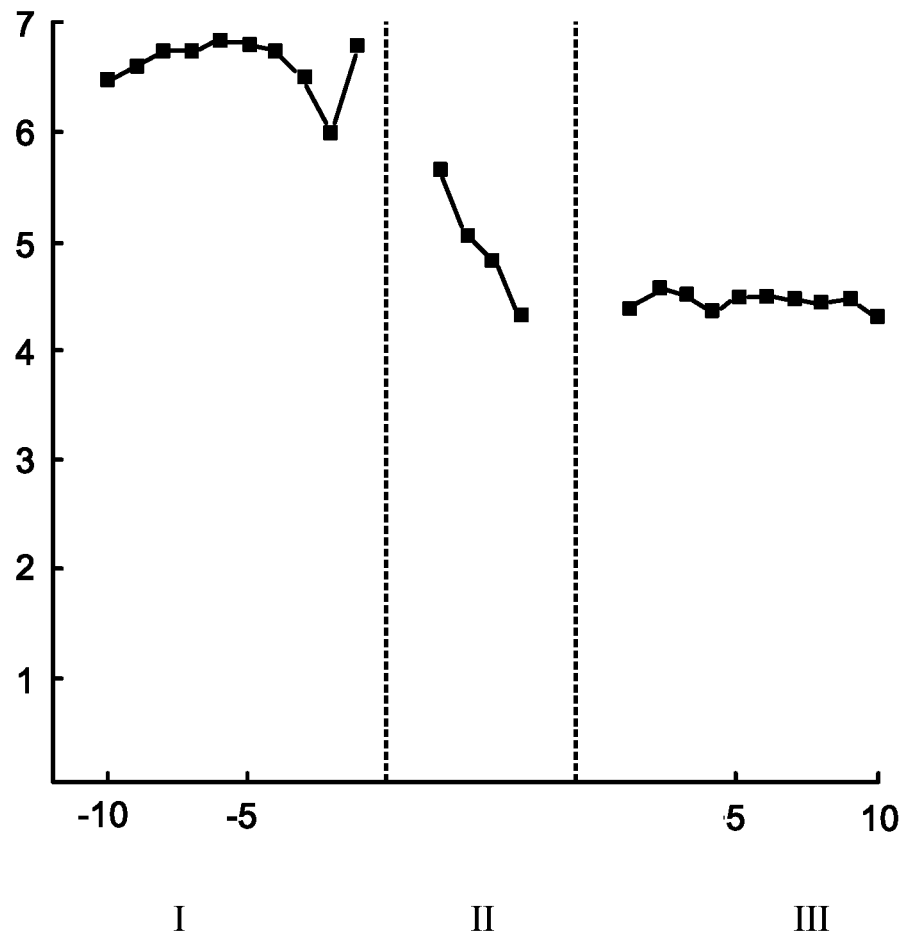
FIG. 5 is a graph depicting typical human ventilation volumes associated with different states of awareness.

An example embodiment of such a sleep efficiency evaluation method is explained in more detail with the aid of FIG. 5, which provides proof of concept of the ability to detect different states of awareness, i.e. a distinction between a subject being awake or asleep. FIG. 5 depicts a graph in which three sleep phases are identified. Phase I is awake, phase II is a transition to a state of sleep and phase III is a state of sleep, with the X-axis displaying time (in minutes) and the Y-axis displaying ventilation of the subject (in l/min). This graph therefore clearly depicts a distinct decrease in ventilation (breathing) volumes upon the subject going from a state of being awake to a state of being asleep. Consequently, the amount of CO2 expelled going from a state of being awake to a state of being asleep is therefore also reduced. The monitored amount of CO2 expelled by a subject under monitoring during a unit period of time can be used as an indicator of whether the subject is awake or asleep. For example, if the amount of CO2 expelled during such a unit period of time exceeds a defined threshold, this may be considered indicative of the subject being awake, whereas if the amount of CO2 expelled during such a unit period of time falls below this defined threshold, this may be considered indicative of the subject being asleep.

Figure 6:
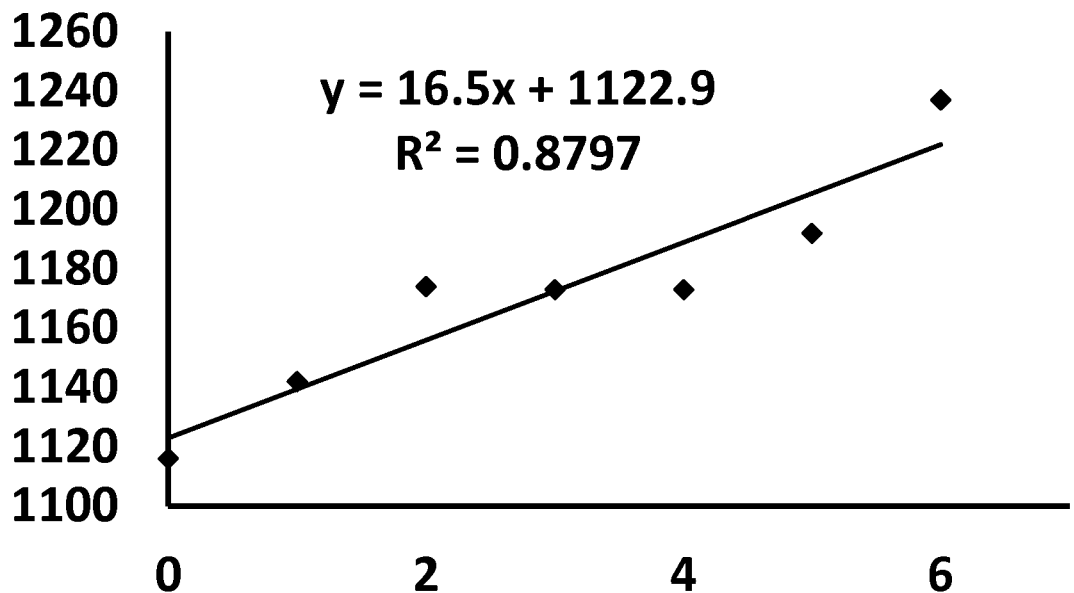
FIG. 6 is a graph depicting measured indoor CO2 levels for a room in which a person is active.
Figure 7:
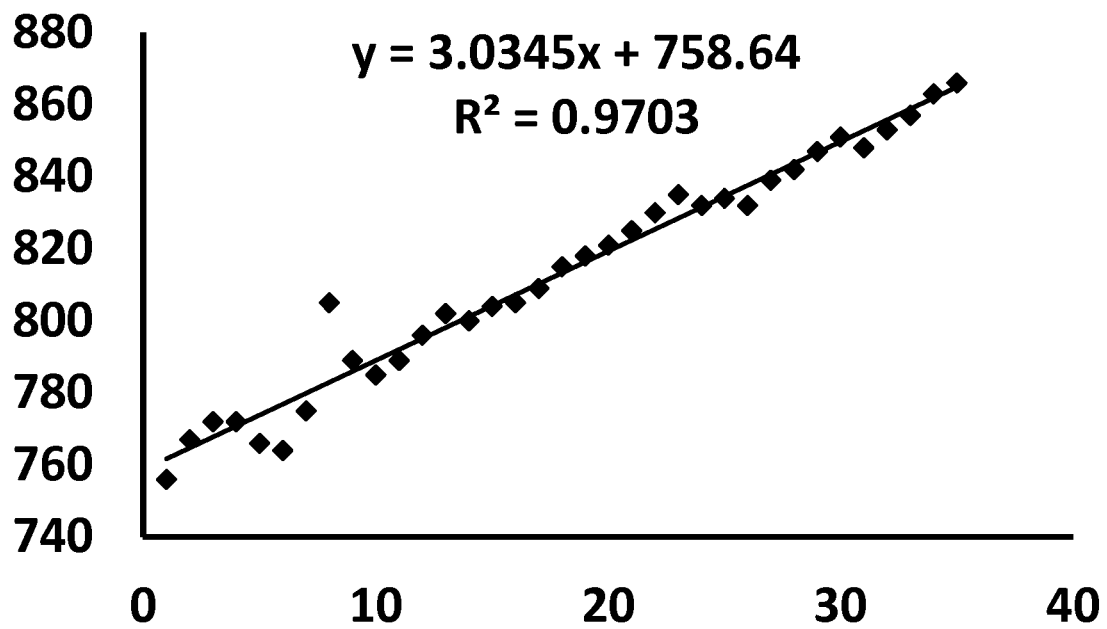
FIG. 7 is a graph depicting measured indoor CO2 levels for a room in which a person is awake but resting.
Figure 8:
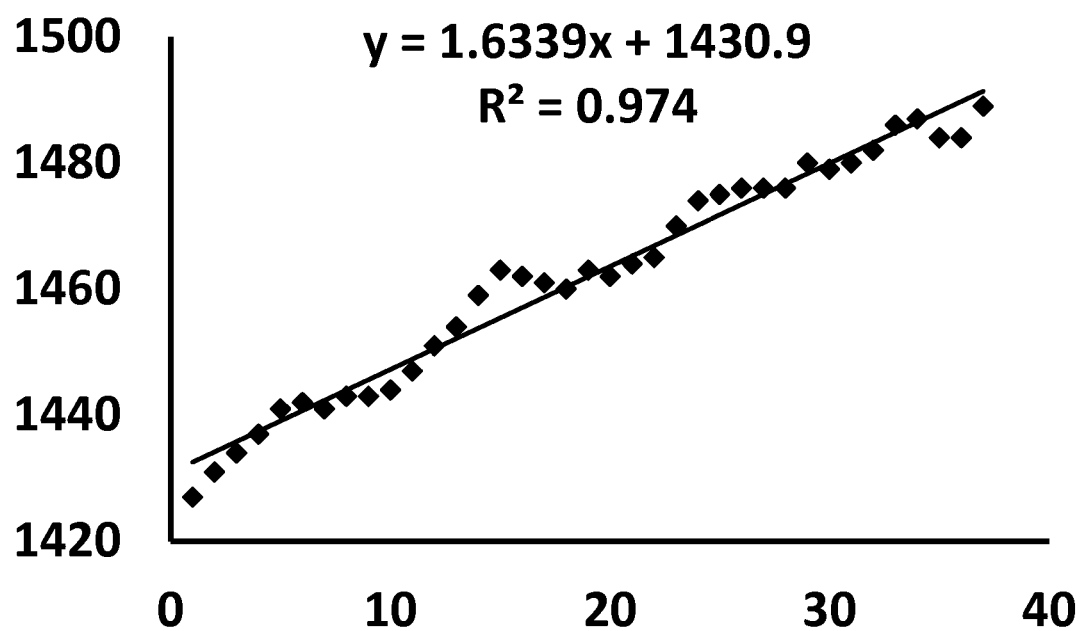
FIG. 8 is a graph depicting measured indoor CO2 levels for a room in which a person is asleep.

The feasibility of using the monitoring of CO2 levels to monitor the sleep of a subject is further demonstrated by FIG. 6-8, in which the levels of CO2 expelled by a subject during exercise (FIG. 6), rest (FIG. 7) and sleep (FIG. 8) were monitored with a CO2 sensor over a period of time within the same confined space (i.e. a space having a constant volume of 29.25 m$^3$), with hermetically sealed windows and doors to minimize the loss of CO2 from the confined space. During exercise, the monitored CO2 levels translated into a rate of CO2 increase of 16.5 ppm/min. In a rest state (i.e. the subject being awake but resting), the monitored CO2 levels translated into a rate of CO2 increase of 3.0 ppm/min, whereas in a sleep state of the subject, the monitored CO2 levels translated into a rate of CO2 increase of 1.6 ppm/min.

As will be immediately understood, the absolute values of these rates of CO2 increase are dependent of several factors such as volume of the confined space, bodyweight and/or lung capacity of the monitored subject, rate of loss of CO2 from the confined space, and so on. However, the data in FIG. 6-8 clearly demonstrates that for a particular subject, a clear difference exists in the rate at which CO2 levels rise in the confined space between the various physical states of the monitored subject. Consequently, it is clearly demonstrated that by determining the rate of increase of the CO2 level and comparing this rate against a defined threshold, a determination can be made about the physical state of the monitored subject, e.g. whether the subject is awake or asleep.

Moreover, it is well-known per se that a person in a light state of sleep produces a higher volume of ventilation (breathing) per unit time compared to a person in a deep state of sleep, such that a distinction between a light sleep and a deep sleep of a monitored subject may also be made by monitoring a rate of increase of CO2 levels in the confined space and comparing the determined rate of increase of CO2 levels in the confined space against a further defined threshold, with a light sleep being detected when the determined rate of increase of CO2 levels in the confined space is above the further defined threshold and a deep sleep being detected when the determined rate of increase of CO2 levels in the confined space is below the further defined threshold.

In an embodiment, the sleep monitoring system 10 may be configured to determine a particular physical state of the monitored subject in accordance with Table 1 (threshold 1 being higher than threshold 2):

TABLE 1

| State | Threshold 1 | Threshold 2 |
| --- | --- | --- |
| Awake | Above | Above |
| Light sleep | Below | Above |
| Deep Sleep | Below | Below |

As previously mentioned, the absolute values of threshold 1 and threshold 2 will depend from a number of factors, such as such as volume of the confined space, bodyweight and/or lung capacity of the monitored subject, rate of loss of CO2 from the confined space, and so on. In an embodiment, the respective thresholds to be applied by the sleep monitoring system 10 may be obtained through calibration of the system. This may be achieved in any suitable manner. For example, at least the CO2 sensor 21, 21' of the sleep monitoring system 10 may be placed within the confined space and used to monitor the subjects over a period of time, e.g. during a night, in which the subjects sleep within the confined space 1. The data collected with the CO2 sensor 21, 21' may be evaluated to identify typical changes in the rate of increase of CO2 levels within the confined space, which typical changes will be indicative of a change in physical state of the subject, e.g. a transition from a state of being awake to a state of light sleep or a transition from a state of light sleep to a state of deep sleep. Consequently, the various physical states can be readily identified in the collected data, such that the applicable values of Threshold 1 and Threshold 2 associated with (transitions between) these various physical states can be readily derived from the collected data. In order to improve the accuracy of the thus extracted thresholds, the data collection during calibration may be repeated a number of times, e.g. over a number of nights. The sleep monitoring system 10 may have a calibration mode that can be user-activated. For example, the sleep monitoring system 10 may comprise a user interface, e.g. on a separate device configured with an app or the like to communicate with the computing device 30 or on the computing device 30 itself, which allows the user to activate the calibration mode, e.g. after installation of the CO2 sensor 21, 21' in the vicinity of the locations, i.e. sleeping regions within the space 1, in which the subjects to be monitored intend to sleep, e.g. different sides of the bed 7.

In an embodiment, the sleep monitoring system 10 is adapted to determine the sleep efficiency of a particular subject being monitored by its associated CO2 sensor 21, 21'. The sleep efficiency SE may be defined as follows:

$$SE = \frac{\Delta T_{sleep}}{\Delta T_{total}} \quad (4)$$

$\Delta T_{total}$ is the total time the subject is attempting to sleep, whereas $\Delta T_{sleep}$ is the total time the subject actually is asleep. $\Delta T_{total}$ may be defined as a first time period initiated by an indication that the subject is attempting to sleep and terminated by an indication that the subject is getting up. The indication that the subject is getting up typically follows an indication that the subject has been asleep although this is not strictly necessary; for example in a scenario where the subject did not manage to sleep at all, such an indication of the subject being asleep would not be obtained.

The total time $\Delta T_{total}$ may be determined in a number of ways. For example, the start point of this period may be determined by collecting an indication with a further sensor that the subject is attempting to sleep. This for example may be a pressure sensor for detecting the subject entering the bed, which pressure sensor for instance may be attached to a pillow or mattress or the like. However, such an indicator may be less accurate if the subject initially engages in relaxing activities before attempting to sleep, such as reading or watching TV. Alternatively, the further sensor may be a light sensor that detects a change in light level in the confined space. In this manner, if the subject switches off a light within the confined space such as a bedside lamp or the TV, this may be interpreted as an indication of the subject attempting to go to sleep, and such an indication may be an accurate indication from which the determination of the time period $\Delta T_{total}$ may be initiated. Similarly, a sound sensor such as a microphone may be used for this purpose, as the user switching off the TV or stopping reading may be detected by a reduction in noise levels within the confined space. In yet another embodiment, the subject may provide a user input on a user input sensor of the sleep monitoring system 10, e.g. on the user interface, to provide a particularly accurate indication of the subject initiating attempting to sleep. The endpoint of the time period $\Delta T_{total}$ may be determined in a similar manner, for example by detecting an alarm going off, by the subject switching on a light, from an increase in the rate at which CO2 is expelled by the subject is determined with the CO2 sensor 21, 21', and so on.

$\Delta T_{sleep}$ may be defined as a second time period initiated by an indication that the subject is asleep and terminated by an indication that the subject is awake that follows the indication that the subject is asleep. In case of a disrupted sleep pattern, the subject may experience a number of periods during which the subject is asleep. In such a scenario, the total period $\Delta T_{sleep}$ that the subject was asleep may be obtained by summing all periods during which it was determined that the subject was asleep.

As will be understood from the foregoing, the total time $\Delta T_{sleep}$ may be determined using the CO2 sensor data collected with the CO2 sensor 21, 21'. For example, the CO2 sensor 21, 21' may periodically sample the CO2 levels in the confined space 1 in which the subject is attempting to sleep, which periodic data may be used to determine the total time $\Delta T_{sleep}$. For example, the total time $\Delta T_{sleep}$ may be determined by counting the number of data points in the periodic data for which the rate of increase of the CO2 level relative to the previously captured data point was below Threshold 1. Other suitable ways of determining $\Delta T_{sleep}$ from the collected sensor data will be immediately apparent to the skilled person.

The sleep monitoring system 10 may be further refined, for example to factor in scenarios in which the monitored subject temporarily leaves the bed, e.g. for a toilet break or the like. To this end, the sleep monitoring system 10 for example may be configured to continue determining the time period ΔTtotal if it is determined that the subject returns to bed within a defined period of time. This may be determined in any suitable manner, e.g. using sensor data provided by the CO2 sensor 21, 21' and/or one or more of the further sensors as previously explained. Other refinement approaches will be apparent to the skilled person. In an embodiment, the sleep monitoring system 10 is further adapted to calculate the sleep onset latency (SOL) for the monitored subject. The sleep onset latency may be defined as the time period between the point in time at which the subject attempts to go to sleep and the point in time at which the subject actually falls asleep. The point in time at which the subject attempts to go to sleep and the may be determined the point in time at which the subject actually falls asleep may be determined as previously explained.

In an embodiment, the sleep monitoring system 10 may be adapted to provide an indication of the calculated sleep efficiency SE, optionally including an indication of the sleep onset latency SOL, on the sensory output device 35 such that the monitored subject may be made aware of his or her sleep efficiency. To this end, the sensory output device 35 may be included in a computing device 30 that is portable, e.g. a tablet device or mobile communications device such as a smart phone, or wearable device, e.g. a smart watch or the like that may be worn by the monitored subject during sleep. This has the further advantage that if the CO2 sensors 21, 21' are separate to the computing device 30, e.g. part of one or more sensor devices, a short range wireless communication between the CO2 sensors 21, 21' and the computing device 30 may be deployed, e.g. NFC or Bluetooth, which may be beneficial in terms of energy efficiency.

The sleep monitoring system 10 may be adapted to build a history of sleep efficiencies to allow evaluation of the sleep history of the subject to be monitored. For example, the processor 31 may be adapted to store sleep monitoring data and/or a sleep efficiency calculated from the sleep monitoring data in the data storage device 33. The sleep monitoring system 10 may comprise a display as the sensory output device 35 on which the sleep history stored in the data storage device 33 may be displayed. In this manner, a history of the sleep efficiency of the monitored subject may be displayed and evaluated, which may provide valuable insights into typical sleep behaviours of the monitored subject. Such insights for instance may be used to determine if certain physical symptoms of the monitored subject may be explained by the sleep efficiency of the monitored subject over a period of time or if certain patterns can be derived from the collected data, e.g. a difference in sleep efficiency between weekdays and weekends, which may indicative of underlying stress-related factors.

Figure 4:
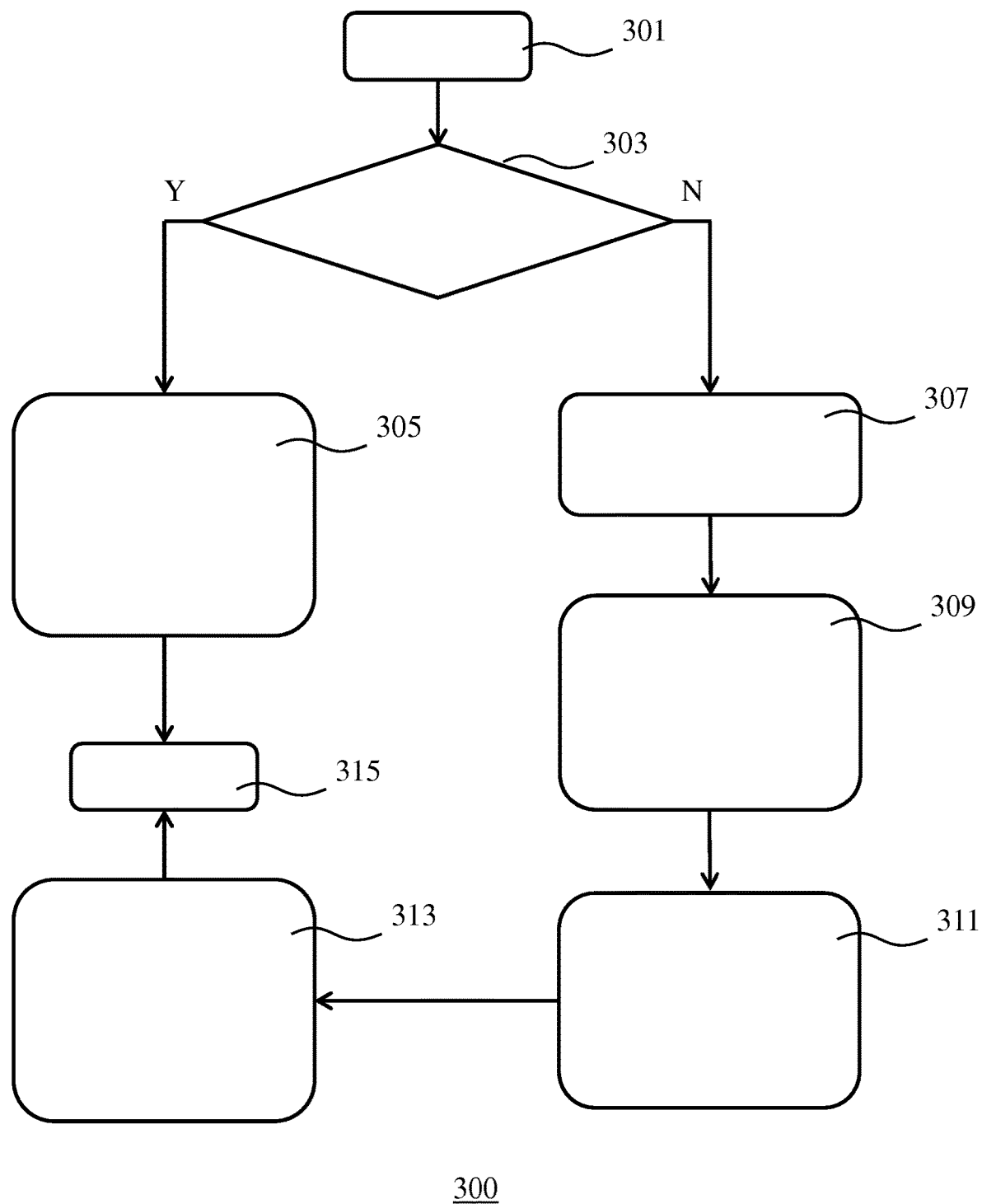
FIG. 4 is a flowchart of an aspect of a sleep monitoring method according to an embodiment.
Figure 9A:
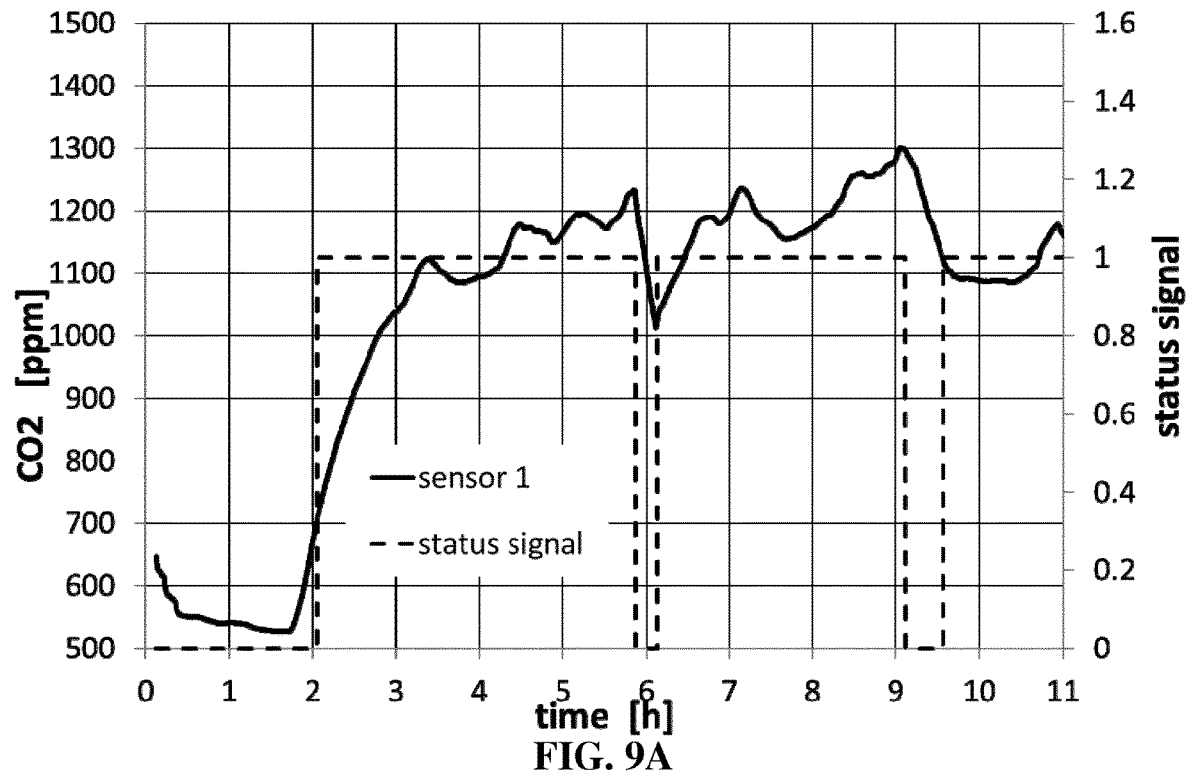
FIG. 9 a graph of CO2 development over 2 nights as monitored by the pair of CO2 sensors of a sleep monitoring system according to an embodiment.
Figure 9B:
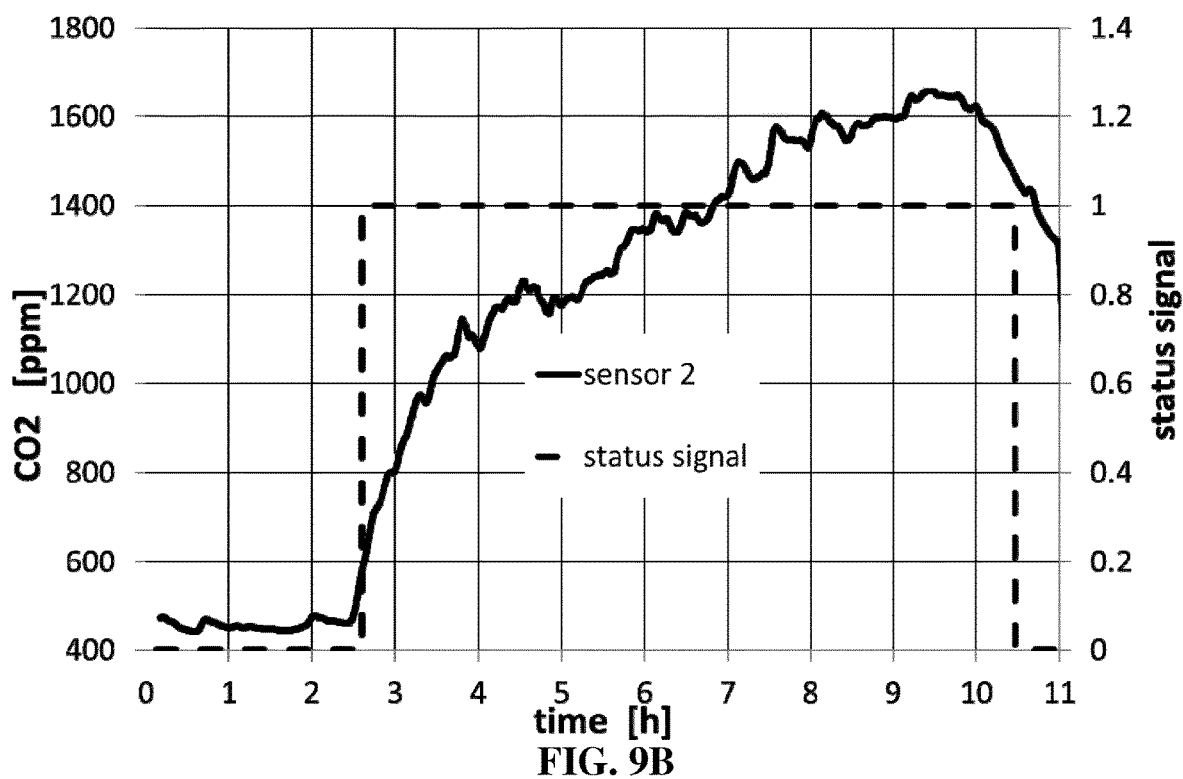

Now, upon returning to FIG. 4, if it is decided in 303 that it is likely that the data collected with the CO2 sensors 21, 21' includes non-negligible crosstalk between the sensors, e.g. because ventilation in the space 1 is insufficient, the method 300 proceeds to 307 in which for the evaluation periods within the datasets collected with each CO2 sensor 21, 21', a linear fit procedure is deployed to divide such an evaluation period into a plurality of linear segments each having a particular slope. This is explained in more detail with the aid of FIG. 9, which shows two graphs, each corresponding to a different day period (i.e. two nights of following days) and in which the data collected with the CO2 sensors 21, 21' during these periods is depicted (solid lines in FIG. 9) The dashed lines in FIG. 9 indicate the selected time intervals an analysis will be performed (status signal value=1). The transition of the signal value from zero to one or from one to zero (vertical dashed lines) indicate changes in the detected CO2 levels indicative of the start (i.e. a sudden rise in the detected CO2 levels) and end (a sudden decrease in the detected CO2 levels) of an evaluation period as explained in more detail above.

Figure 10:
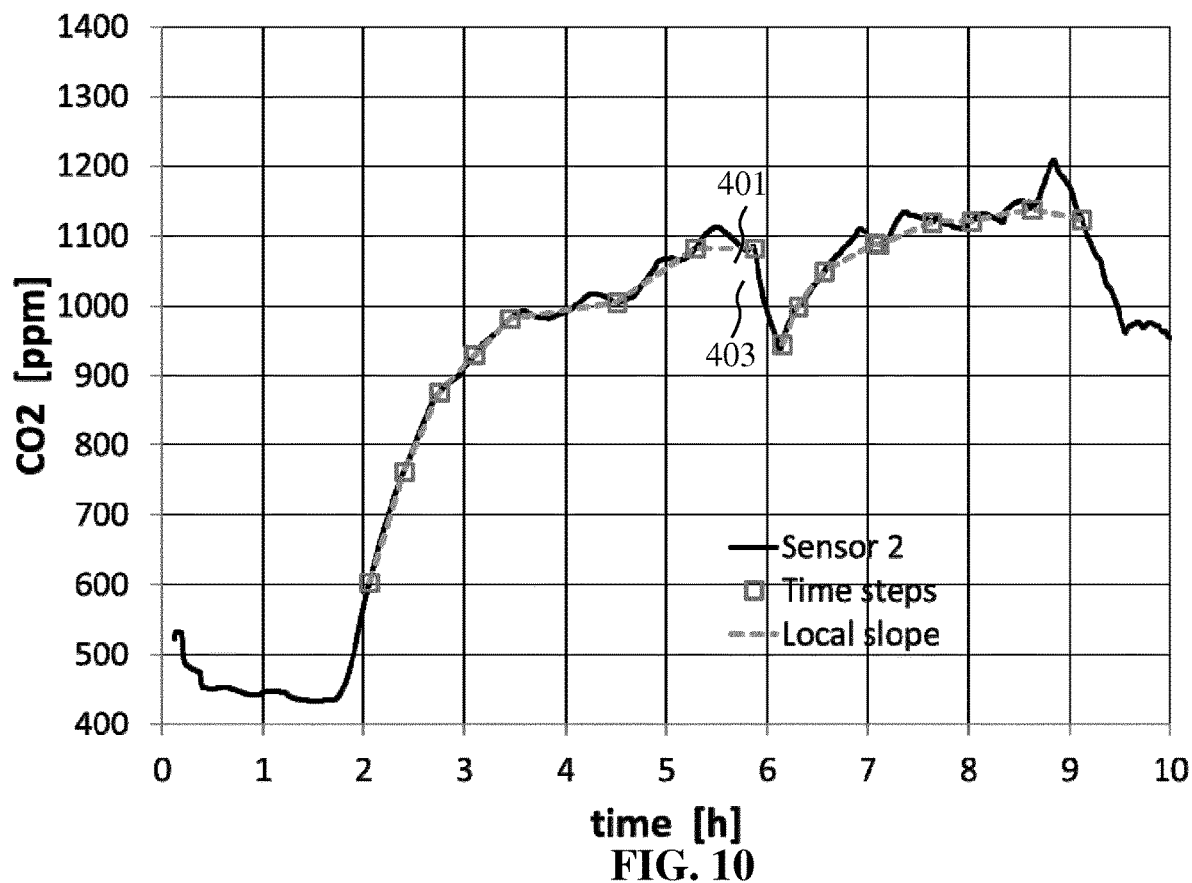
FIG. 10 is a graph depicting a linear fit method deployed on CO2 data captured with a CO2 sensor of a sleep monitoring system according to an embodiment.

For each evaluation period, a linear fit as depicted in FIG. 10 is deployed. As can be seen in FIG. 10, the data 401 collected with a CO2 sensor 21, 21' at sample rate SR as explained above is divided into a number of time intervals of constant duration as indicated by the squares. Each such a time interval is defined by a start point $t_s$, which is one of the (averaged) data samples of the data 401 and an end point $t_e$, which is another one of the (averaged) data samples of the data 401, wherein the start and end points are defined such that each time interval encloses N intermediate data samples of the data 401. Each time interval may have the same duration although this is not strictly necessary. Each time interval preferably has a duration of at least two times the period over which a plurality of data points is collected with a CO2 sensor 21, 21' for data averaging purposes as previously explained, and more preferably at least four times this period. For each time interval, the slope S for the time interval may be determined as:

$$S(t_s)=(CO2(t_e)-CO2(t_s))/(t_e-t_s) \qquad (5)$$

In equation 5, $CO2(t_e)$ and $CO2(t_s)$ are the CO2 levels determined with the CO2 sensor producing the data 401 at the endpoint and start point of the time interval respectively. In this manner, a linear fit curve 403 may be obtained, which is composed of the linearized time intervals, with each time interval having its slope as determined in accordance with equation 5.

Figure 11:
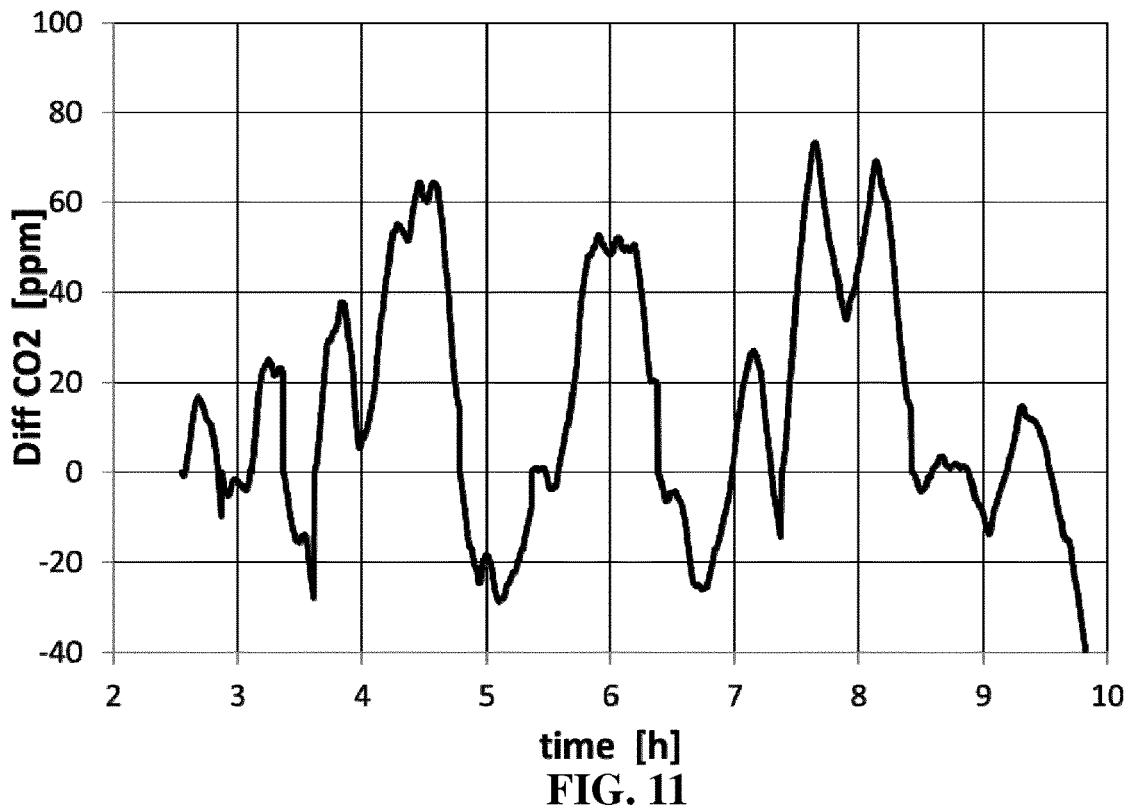
FIG. 11 is a graph depicting a difference between actual monitored CO2 concentrations and a linear fit deployed on CO2 data captured with a CO2 sensor of a sleep monitoring system according to an embodiment.

Next, the method 300 proceeds to 309 in which a difference between the actual data 401 collected with a particular CO2 sensor 21, 21' and its linear fit curve 403 is determined. FIG. 11 depicts a graph in which this difference function is visualized. Such a difference function Diff may be expressed by equation 6:

$$\text{Diff}_k(t)=CO2_k(t)-(CO2_k(t_s)+S(t_s)*(t-t_s)) \qquad (6)$$

In equation 6, $\text{Diff}_k$ (t) is the difference for CO2 sensor k between the CO2 level determined at point in time t ($CO2_k$ (t)), $CO2_k(t_s)$ is the CO2 level determined with CO2 sensor k at the start point $t_s$ of this time interval and $S(t_s)$ is the slope of this time interval as determined with equation 5.

These difference values are already correlated to sleeping activity of the subjects sleeping in the space 1, as will be readily understood by the skilled person. However, in order to individualize this data, the crosstalk contribution to each dataset needs to be identified. To this end, for each CO2 sensor 21, 21' a modified activity signal mAC is derived, which includes information obtain from the difference function Diff for the other CO2 sensor. For this purpose, the method 300 proceeds to 311 in which an averaged difference function [Ave(Diff$k'$ (t))] of the other CO2 sensor (here labeled k') is determined. The aim of this difference function Ave(Diff$k'$ (t)) is to improve decoupling of the contribution of the second person to the CO2 signal produced by sensor 21 that is used to determine sleep activity of the first person. This is done by making use of the information of sensor 21' which is closer to the second person. But due to the fact that the CO2 signal of sensor 21' also includes a contribution of the other (first) person, a specific measure is needed to decouple these signals.

Because of the larger distance of sensor 21' to the 1' person, the signal amplitude of the CO2 signal of sensor 21' due to the contribution of the 1' person and the steepness of the signal change are smaller. Consequently, an averaged value of the difference for CO2 sensor k' [Diffk' (t)] together with a weighting factor β is used for the correction. The product of Diffk' (t) and 13 is added to the difference function $Diff_k(t)$:

$$mACk = Diffk(t) + \beta * Ave(Diffk'(t)) \quad (7)$$

Figure 12:
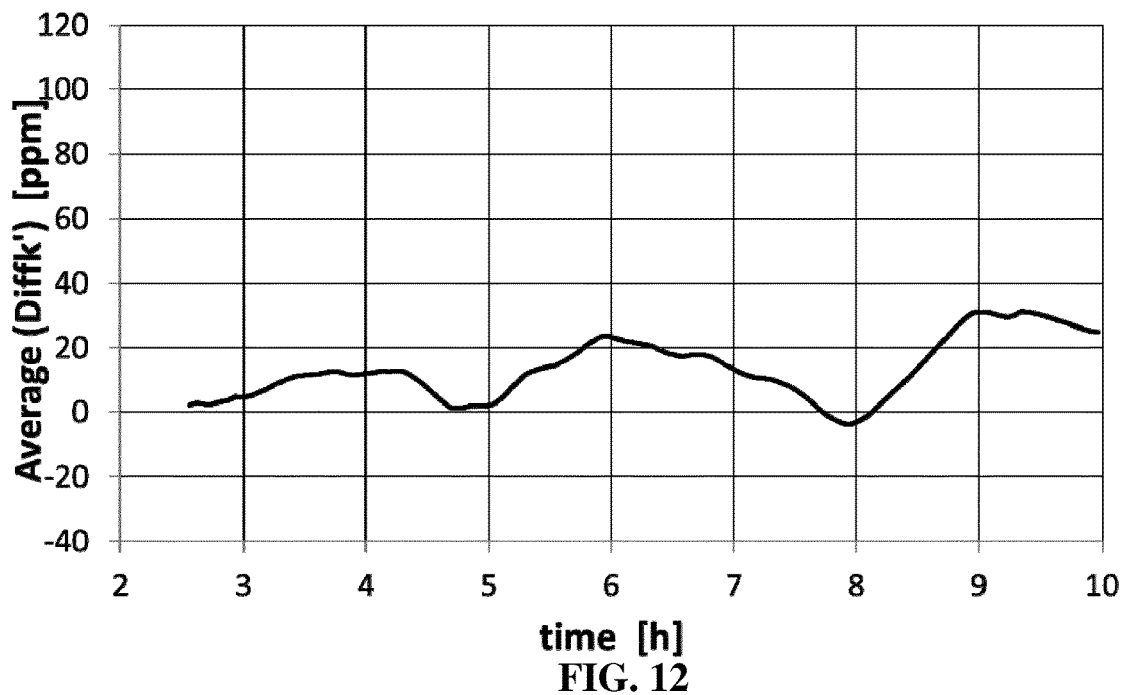
FIG. 12 is a graph depicting an averaged difference between actual monitored CO2 concentrations and a linear fit deployed on CO2 data captured with a CO2 sensor of a sleep monitoring system according to an embodiment.

As explained above, the averaging of the difference functions Diffk(t) and Diffk' (t) preferably is performed at a time constant T that is larger than the averaging period to obtain an averaged sample point in the data 401 ($t_{ave}$) as previously explained. T should be more than 1.5 times this averaging period and preferably lies between 4-6 times this averaging period. An example of such an averaged signal Ave($Diff_k'$ (t)) of sensor 21' is given in FIG. 12; the used time constant is $T=5*t_{ave}$.

In equation (7), β is a scaling factor quantifying the amount of crosstalk between the CO2 sensors 21, 21'. A typical value of scaling factor β is in a range of 0.2 to 0.8 and in an example embodiment, β=0.5. This scaling factor may be determined empirically and may factor in actual ventilation conditions in the space 1; for example, in case of no ventilation, a higher scaling factor β may be deployed as compared to a situation in which some ventilation reduces the crosstalk between the CO2 sensors 21, 21'.

Next, the method 300 proceeds to 313 in which the sleep efficiency evaluation for each subject in the space 1 is performed based on the mAC signals of the corresponding CO2 sensors 21, 21' as obtained with equation 7. Each mAC signal may be evaluated in accordance with the evaluation method previously described in more detail for step 305 of the method 300. Alternatively or additionally, each mAC signal may be further analyzed by applying a threshold value TH to the data of this signal in order to compensate for noise and fluctuations in sensitivity of the corresponding CO2 sensor, for example by a subject associated with that sensor turning over in the bed 7 such that less CO2 may be directed towards the corresponding CO2 sensor. In this embodiment, the subject's activity time $T_{AC}$ during his or her stay in the space 1 may be calculated as follows:

$$T_{AC,k} = t(mAC_k - TH_k > 0)/(t_{end} - t_{start}) \quad (8)$$

In equation 8, $t_{start}$ and $t_{end}$ are the start time and end time of the evaluation period respectively.

The threshold value $TH_k$ may be determined based on a minimum value of $mAC_k$. For example, the absolute value of this minimum multiplied with a scaling factor γ may be used to define $TH_k$:

$$TH_k = \gamma * Abs[Min(AC_k(t)] \quad (9)$$

The scaling factor γ may be empirically determined and should be larger than 0.5. In a preferred embodiment, the value of γ is about 1.5. However, in order to improve the accuracy of the sleep evaluation procedure, the value of $TH_k$ may have a defined lower limit which is used instead of γ if γ become smaller than this lower limit. For example, the lower limit of $TH_k$ may be defined to be 15 ppm. Alternatively, this lower limit may be defined as 20 ppm*Q/V, in which Q is the ventilation rate and V is the volume of the space 1. Other suitable definitions of this lower limit will be immediately apparent to the skilled person.

Figure 13:
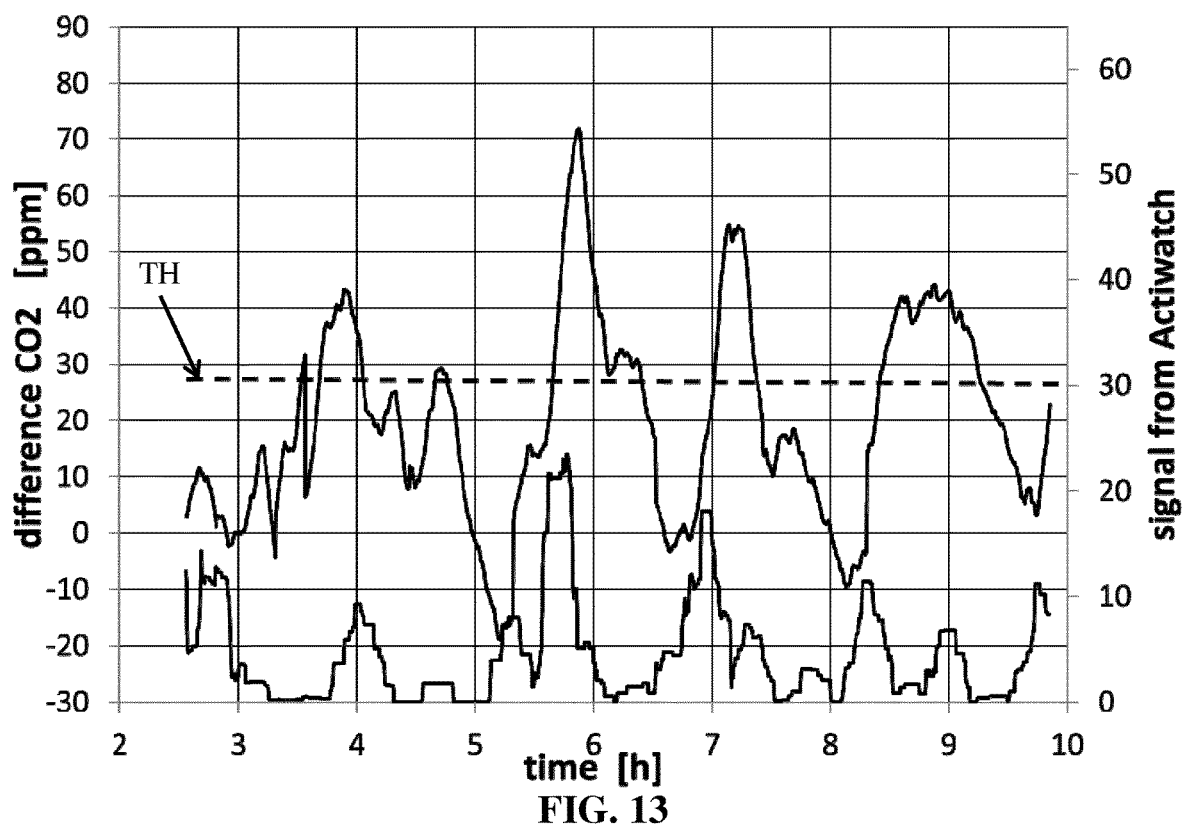
FIG. 13 is a graph depicting a comparison between crosstalk-corrected CO2 monitoring data obtained with a CO2 sensor of a sleep monitoring system according to an embodiment and sleep pattern data obtained with a wearable sleep monitoring device (Philips Actiwatch).

Proof of concept was demonstrated with a sleep monitoring system 10 according to an embodiment in which the CO2 emissions of two subjects as captured with CO2 sensors 21, 21' was compared against sleep activity data obtained with a calibrated wearable sleep monitoring device (Philips Actiwatch) worn by each of the subjects. FIG. 13 depicts the mAC signal (top signal) of one of the CO2 sensors 21, 21' and the Actiwatch signal (bottom signal) obtain from the subject monitored by this CO2 sensor. The threshold TH applied to the mAC signal is indicated by the block arrow labelled TH. Table 2 lists the $T_{AC}$ values as determined with the CO2 sensors 21, 21' (labelled $T_{AC,1}$ and $T_{AC,2}$ respectively) and the Actiwatch (labelled AW1 and AW2 respectively) for three different days.

TABLE 2

|  | $T_{AC,1}$ | AW1 | $T_{AC,2}$ | AW2 | $t_{end}$-$t_{start}$ |
| --- | --- | --- | --- | --- | --- |
| Day 1 | 0.22 | 0.28 | 0.28 | 0.30 | 3.5 h |
| Day 2 | 0.26 | 0.27 | 0.34 | 0.34 | 7.25 h |
| Day 3 | 0.34 | 0.35 | 0.27 | 0.27 | 7.0 h |

As can be seen from both FIG. 13 and Table 2, an excellent correlation exists between the data collected with the sleep monitoring system 10 and the Actiwatch data, especially for data collected over longer periods. This clearly demonstrates the ability of the sleep monitoring system 10 to accurately monitor individual sleep activity in the presence of crosstalk between the CO2 sensors 21, 21'.

At this point, it is noted that the above described sleep evaluation methods may be further enhanced as will be apparent to the skilled person. For example, the sleep monitoring system 10 may incorporate further sensors such as absolute humidity sensors, which humidity information may be used to reduce noise on the data collected with the CO2 sensors 21, 21'. Similarly, in case of a ventilated space 1, outdoor fluctuations in the CO2 levels may affect such noise levels. The sleep monitoring system 10 may be adapted to obtain actual outdoor CO2 levels, e.g. from a remote Internet service providing such levels, in order to correct the data collected with the CO2 sensors 21, 21' accordingly.

Aspects of the present invention may be embodied as sleep monitoring system 10 and a method 100 for monitoring the sleep of a subject. Aspects of the present invention may take the form of a computer program product embodied in one or more computer-readable medium(s) having computer readable program code embodied thereon. The code typically embodies computer-readable program instructions for, when executed on a processor 31 of such a sleep monitoring system 10, implementing the sleep monitoring method 100.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor 31 may be written in any combination of one or more programming languages, including an object oriented programming language such as Java, Smalltalk, C++ or the like and conventional procedural programming languages, such as the "C" programming language or similar programming languages. The program code may execute entirely on the processor 31 as a stand-alone software package, e.g. an app, or may be executed partly on the processor 31 and partly on a remote server. In the latter scenario, the remote server may be connected to the sleep monitoring system 10 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the processor 31 of the sleep monitoring system 10, such that the instructions create means for implementing the functions/acts specified in the flowchart and/or block diagram block or blocks. These computer program instructions may also be stored in a computer-readable medium that can direct the sleep monitoring system 10 to function in a particular manner.

The computer program instructions may be loaded onto the processor 31 to cause a series of operational steps to be performed on the processor 31, to produce a computer-implemented process such that the instructions which execute on the processor 31 provide processes for implementing the functions/acts specified in the flowchart and/or block diagram block or blocks. The computer program product may form part of the sleep monitoring system 10, e.g. may be installed on the sleep monitoring system 10.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sleep monitoring system for monitoring the sleep of a pair of subjects, comprising a pair of CO2 sensors for mounting in different sleeping regions within a space and positioned to detect CO2 emissions by a subject, and a processor communicatively coupled to the pair of CO2 sensors, wherein the processor is adapted to, for each CO2 sensor in a particular sleeping region:
 monitor a CO2 concentration from sensor data produced by the CO2 sensor in said particular sleeping region to detect a presence of the subject in said sleeping region;
 register the monitored CO2 concentration upon detecting said presence;
 determine a degree of crosstalk between said CO2 sensors upon detecting said presence; and
 derive sleep pattern information for said subject from the registered CO2 concentration during said presence as a function of the determined degree of crosstalk, wherein the sleep pattern information comprises at least an indication that the subject is awake and an indication that the subject is asleep.

2. The sleep monitoring system of claim 1, wherein the processor is adapted to determine a minimum CO2 concentration and a maximum CO2 concentration in the monitored CO2 concentration and ignore said crosstalk in deriving the sleep pattern for said subject if a difference between the minimum CO2 concentration and the maximum CO2 concentration is below a defined threshold.

3. The sleep monitoring system of claim 1, wherein the processor is adapted to estimate said crosstalk in deriving the sleep pattern for said subject in response to a user instruction indicating a degree of ventilation of said space.

4. The sleep monitoring system of claim 1, wherein the processor is adapted to derive sleep pattern information for said subject from the registered CO2 concentration by:
 identifying that the subject is awake when a rate of increase in said registered CO2 concentration is greater than a first threshold;
 identifying a light sleep phase of the subject when a rate of increase in said registered CO2 concentration is between the first threshold and a second threshold; and
 identify a deep sleep phase of the subject when a rate of increase in said registered CO2 concentration is below the second threshold.

5. The sleep monitoring system of claim 1, wherein the processor is adapted to, for each CO2 sensor in a particular sleeping region:

initiate a period during which the CO2 concentration is monitored for sleep evaluation purposes upon detection of said presence;

terminate said period upon detection of said subject leaving said particular sleeping region; and determine at least one rate of CO2 concentration change during said period.

6. The sleep monitoring system of claim 5, wherein the processor is adapted to:

detect said presence by detection of an increase in the CO2 concentration in said particular region exceeding a first further threshold; and detect said subject leaving said particular sleeping region by detection of a decrease in the CO2 concentration exceeding a second further threshold.

7. The sleep monitoring system of claim 1, wherein the processor is adapted to, for each CO2 sensor:

periodically sample the CO2 concentration in said particular sleeping region; and derive the at least one rate of CO2 concentration change in the registered CO2 concentration by a linear fit based on the periodic CO2 concentration samples taken during registering said CO2 concentration.

8. The sleep monitoring system of claim 7, wherein the processor is adapted to periodically sample the CO2 concentration at a point in time by averaging a plurality of CO2 measurements with the CO2 sensor in said particular sleeping region in a time period associated with said point in time, said time period being at most half a sampling period of the periodic sampling.

9. The sleep monitoring system of claim 7, wherein the processor is further adapted to, for each registered monitored CO2 concentration:

determine a difference function between an actual monitored CO2 concentration and said linear fit; and determine a crosstalk contribution to said registered monitored CO2 concentration based on a difference between the difference function of said registered monitored CO2 concentration and a product of an averaged difference function of the other registered monitored CO2 concentration and a scaling factor, said scaling factor being dependent of at least one of a volume of said space and a rate of ventilation of said space.

10. The sleep monitoring system of claim 1, wherein the processor is adapted to monitor a CO2 concentration from sensor data produced by both CO2 sensors upon detecting the presence of a subject in one of said sleeping regions.

11. A method for monitoring the sleep of a pair of subjects in different sleeping regions within a space, each sleeping region comprising a CO2 sensor positioned to detect CO2 emissions by a subject, the method comprising, for each CO2 sensor:

monitoring a CO2 concentration from sensor data produced by the CO2 sensor in said particular sleeping region to detect a presence of the subject in said sleeping region;

registering the monitored CO2 concentration upon detecting said presence;

determining a degree of crosstalk between said CO2 sensors upon detecting said presence; and deriving sleep pattern information for said presence from the registered CO2 concentration during said presence as a function of the determined degree of crosstalk, wherein the sleep pattern information comprises at least an indication that the subject is awake and an indication that the subject is asleep.

12. The method of claim 11, further comprising, for each CO2 sensor in a particular region:

initiating a period during which the CO2 concentration is monitored for sleep evaluation purposes upon detecting said presence, preferably by detection of an increase in the CO2 concentration in said particular region exceeding a first further threshold;

terminating said period upon detecting said presence leaving said particular region, preferably by detection of a decrease in the CO2 concentration exceeding a second further threshold; and determining at least one rate of CO2 concentration change during said period.

13. The method of claim 11, further comprising:

periodically sampling the CO2 concentration in said particular region, preferably by averaging a plurality of CO2 measurements with the CO2 sensor in said particular region in a time period associated with said point in time, said time period being at most half a sampling period of the periodic sampling; and deriving the at least one rate of CO2 concentration change in the registered CO2 concentration by a linear fit based on the periodic CO2 concentration samples taken during registering said CO2 concentration.

14. The method of claim 13, further comprising, for each registered CO2 concentration:

determining a difference function between an actual monitored CO2 concentration and said linear fit; and determining a crosstalk contribution to said registered monitored CO2 concentration based on a difference between the difference function of said registered monitored CO2 concentration and a product of an averaged difference function of the other registered monitored CO2 concentration and a scaling factor, said scaling factor being dependent of at least one of a volume of said space and a rate of ventilation of said space.

15. A computer program product comprising a computer readable storage medium having computer readable program instructions embodied therewith for, when executed on a processor of a sleep monitoring system of claim 1, cause the processor to implement the method.

* * * * *